United States Patent
Rabinovitz et al.

(10) Patent No.: US 10,102,334 B2
(45) Date of Patent: Oct. 16, 2018

(54) SYSTEM AND METHOD FOR AUTOMATIC NAVIGATION OF A CAPSULE BASED ON IMAGE STREAM CAPTURED IN-VIVO

(75) Inventors: Elisha Rabinovitz, Haifa (IL); Ori Braun, Palo Alto, CA (US); Yaniv Ben Zriham, Binyamina (IL); Jeremy Pinchas Gerber, Netanya (IL); Gavriel J. Iddan, Haifa (IL); Eli Horn, Motzkin (IL)

(73) Assignee: GIVEN IMAGING LTD., Yoqneam (IL)

( * ) Notice: Subject to any disclaimer, the term of this patent is extended or adjusted under 35 U.S.C. 154(b) by 381 days.

(21) Appl. No.: 13/976,891

(22) PCT Filed: Dec. 29, 2011

(86) PCT No.: PCT/IL2011/000972
§ 371 (c)(1),
(2), (4) Date: Jul. 31, 2013

(87) PCT Pub. No.: WO2012/090197
PCT Pub. Date: Jul. 5, 2012

(65) Prior Publication Data
US 2013/0304446 A1    Nov. 14, 2013

Related U.S. Application Data

(60) Provisional application No. 61/428,332, filed on Dec. 30, 2010.

(51) Int. Cl.
*G06F 19/12* (2011.01)
*G06T 7/00* (2017.01)

(52) U.S. Cl.
CPC ............ *G06F 19/12* (2013.01); *G06T 7/0012* (2013.01); *G06T 2207/10016* (2013.01); *G06T 2207/10068* (2013.01); *G06T 2207/30028* (2013.01); *G06T 2207/30092* (2013.01)

(58) Field of Classification Search
None
See application file for complete search history.

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |
| 5,993,378 A | 11/1999 | Lemelson | |
| 6,240,312 B1 | 5/2001 | Alfano et al. | |
| 6,493,649 B1 | 12/2002 | Jones et al. | |
| 6,778,846 B1 | 8/2004 | Martinez et al. | |
| 6,950,690 B1 | 9/2005 | Meron et al. | |
| 7,009,634 B2 | 3/2006 | Iddan et al. | |
| 7,032,600 B2 | 4/2006 | Fukuda et al. | |
| 7,083,578 B2 | 8/2006 | Lewkowicz et al. | |
| 7,343,036 B2 | 3/2008 | Kleen et al. | |
| 7,468,044 B2 | 12/2008 | Iddan | |
| 7,585,283 B2 | 9/2009 | Kraizer et al. | |
| 7,822,463 B2 | 10/2010 | Meron et al. | |
| 7,901,366 B2 | 3/2011 | Iddan | |
| 7,907,986 B2 | 3/2011 | Lewkowicz et al. | |
| 7,995,798 B2 | 8/2011 | Krupnik et al. | |
| 8,335,362 B2 | 12/2012 | Vilarino et al. | |
| 8,394,034 B2 | 3/2013 | Iddan et al. | |
| 8,396,327 B2 | 3/2013 | Spyridonos et al. | |
| 8,396,563 B2 | 3/2013 | Reinke et al. | |
| 8,428,685 B2 | 4/2013 | Swain et al. | |
| 2002/0103417 A1 | 8/2002 | Gazdzinski | |
| 2002/0165592 A1 | 11/2002 | Glukhovsky et al. | |
| 2003/0045790 A1 | 3/2003 | Lewkowicz et al. | |
| 2005/0228259 A1 | 10/2005 | Glukhovsky et al. | |
| 2005/0256430 A1 | 11/2005 | Lewkowicz et al. | |
| 2005/0272972 A1 | 12/2005 | Iddan | |
| 2007/0015967 A1 | 1/2007 | Boulais et al. | |
| 2007/0255087 A1 | 11/2007 | Minai | |
| 2008/0045792 A1 | 2/2008 | Shimizu et al. | |

(Continued)

FOREIGN PATENT DOCUMENTS

| | | |
|---|---|---|
| JP | 04-022325 | 1/1992 |
| WO | WO 2012/127469 | 9/2012 |

OTHER PUBLICATIONS

McCaffrey, "Swallowable-capsule technology," Pervasive computing, IEEE, vol. 7.1, p. 23-29, 2008.*

(Continued)

*Primary Examiner* — G Steven Vanni
(74) *Attorney, Agent, or Firm* — Pearl Cohen Zedek Latzer Baratz LLP

(57) ABSTRACT

A system and method for automatically navigating an in vivo imaging capsule in a body lumen. The system comprises an imaging capsule including an imager, optional pressure sensor for producing data of forces acting on the imaging capsule in vivo, and a transmitter to transmit image, positioning and pressure data from the capsule to an external unit. A positioning system for providing current position data of the capsule in vivo may be included in the capsule and/or external to it. External magnets may generate a magnetic field to scan a body lumen by causing a predetermined motion pattern of the imaging capsule within a region proximate to its current position, and generate a driving force to propel the imaging capsule according to a calculated target direction vector. A processor may calculate a target direction vector for propelling the imaging capsule based, on unique patterns identifiable in one or more images.

18 Claims, 6 Drawing Sheets

(56) References Cited

U.S. PATENT DOCUMENTS

| | | |
|---|---|---|
| 2008/0199065 A1 | 8/2008 | Swain |
| 2008/0262303 A1 | 10/2008 | Minai et al. |
| 2009/0131784 A1 | 5/2009 | Betesh |
| 2009/0318760 A1 | 12/2009 | Pascal et al. |
| 2009/0318761 A1 | 12/2009 | Rabinovitz |
| 2010/0010306 A1 | 1/2010 | Kawano et al. |
| 2010/0121225 A1 | 5/2010 | Lewkowicz et al. |
| 2010/0268025 A1 | 10/2010 | Belson |
| 2011/0060189 A1 | 3/2011 | Belson |
| 2011/0301497 A1 | 12/2011 | Shachar et al. |
| 2012/0149981 A1 | 6/2012 | Khait et al. |

OTHER PUBLICATIONS

Alomainy, "Modeling and Characterization of Biotelemetric Radio Channel From Ingested Implants Considering Organ Contents," IEEE Transactions on Antennas and Propagation, vol. 57(4), p. 999-1005, Apr. 2009.*

Szczypinski, "Model of deformable rings for aiding the wireless capsule endoscopy video interpretation and reporting," In Computer Vision and Graphics, vol. 32 of Computational Imaging and Vision, Springer, Netherlands, p. 167-172, 2006.*

* cited by examiner

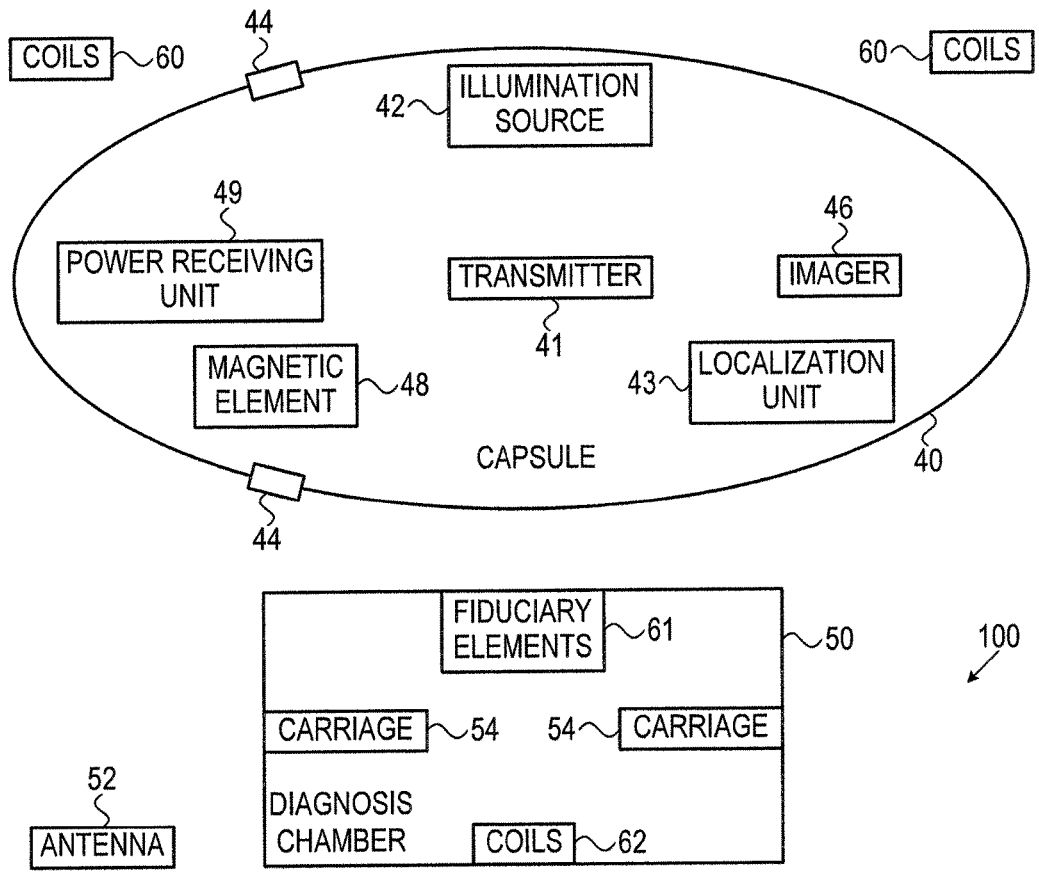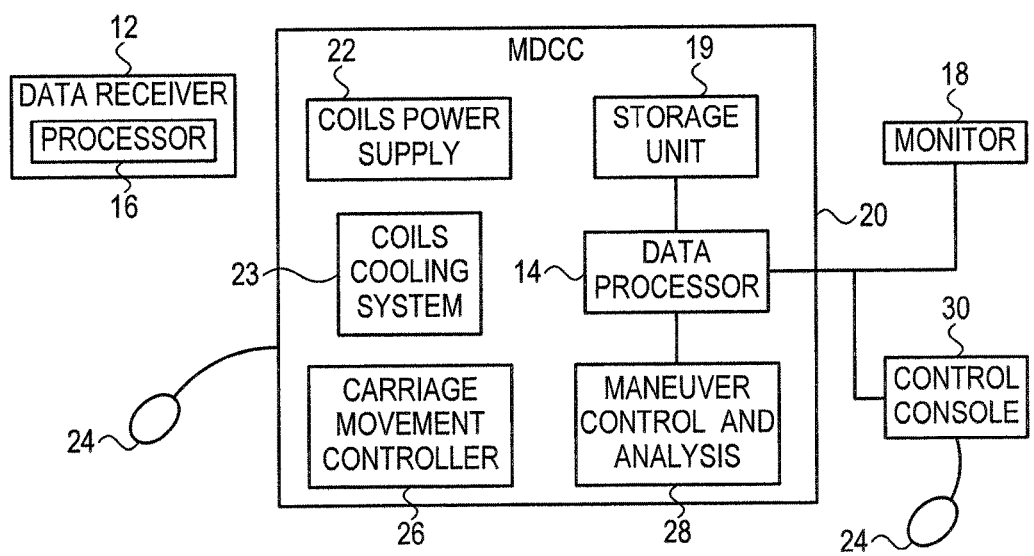
FIG. 1

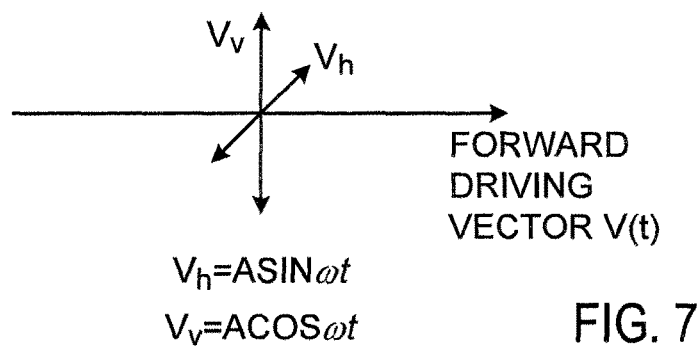
$V_h = A\text{SIN}\omega t$
$V_v = A\text{COS}\omega t$
FIG. 7
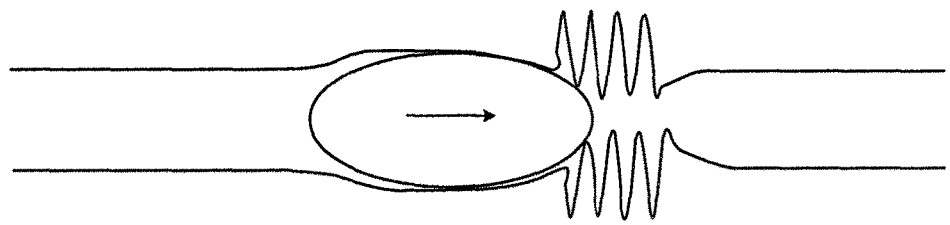
FIG. 8A: CAPSULE DRAGS TISSUE AS IT MOVES FORWARD
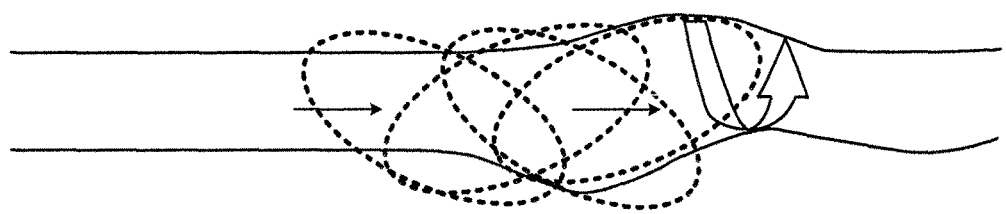
FIG. 8B: CAPSULE MOVES FORWARDS WITH SUPERIMPOSED CONDICAL MOTION PREVENTING TISSUE DRAG

SYSTEM AND METHOD FOR AUTOMATIC NAVIGATION OF A CAPSULE BASED ON IMAGE STREAM CAPTURED IN-VIVO

CROSS-REFERENCE TO RELATED APPLICATIONS

This application is a National Phase Application of PCT International Application No. PCT/IL2011/000972, entitled "SYSTEM AND METHOD FOR AUTOMATIC NAVIGATION OF A CAPSULE BASED ON IMAGE STREAM CAPTURED IN-VIVO", International Filing Date Dec. 29, 2011, published on Jul. 5, 2012 as International Publication No. WO 2012/090197, which in turn claims priority from U.S. Provisional Patent Application No. 61/428,332, filed Dec. 30, 2010, both of which are incorporated herein by reference in their entirety.

FIELD OF THE INVENTION

The present invention relates to systems and methods for automatic and semi-automatic navigation of in vivo imaging capsule in a three-dimensional space allowing six degrees of freedom. More specifically, the present invention relates to systems and methods for automatic and semi-automatic navigation of in vivo imaging capsule in six degrees of freedom based on data captured in-vivo.

BACKGROUND OF THE INVENTION

An in-vivo imaging system which is carried by an ingestible capsule may be used to image lumens within a patient's body, such as, for example, the gastrointestinal (GI) tract. The imaging system captures and transmits images of the passage or cavity to an external device, such as a recording device, while passing through the body. The images, when combined in sequence, may form a moving image stream of the passage.

As a passive system with no active maneuvering capability once ingested, the capsule is carried throughout the entire GI system by natural peristalsis, while the orientation within the GI tract is random and uncontrollable. The capsule can neither be advanced forward to skip over regions that are not of interest, nor delayed or reoriented to provide a more in-depth view (e.g., closer examination) of observed pathologies. The latter function is particularly important, as the mucosal surface of the GI tract is not smooth and often requires images of interest to be illuminated and visualized from various angles.

Magnetically maneuverable capsule endoscopy systems are disclosed in U.S. patent application Ser. No. 12/963,502 to Shachar et al. and in U.S. Provisional Patent Application No. 61/420,937 to Khait et al.

SUMMARY OF THE INVENTION

Embodiments of the invention may provide a system and method for automatic navigation through an anatomical section of a body lumen. The method may include, for example, receiving in vivo images of the body lumen from the imaging capsule, and receiving current position data of the imaging capsule. In some cases, for example if the images are clear and provide a detectable view of the lumen opening or the direction of the tissue wrinkles, a target direction vector may be calculated based on the received images. If no target direction vector may be calculated due to turbid, unclear images, or images which depict a close view of the tissue walls instead of the tissue lumen opening, a local scan of the body lumen may be generated, for example by inducing a predetermined motion pattern of the imaging capsule within a region proximate to its current position. Pressure forces acting on the imaging capsule during the local scan may be sensed, for example using pressure sensors located on the housing surrounding the capsule. A target direction vector for navigating the imaging capsule may be determined, for example by determining the direction which induces the minimal pressure force on the capsule as sensed during the local scan. A driving force to navigate the imaging capsule in the determined direction vector may be generated, for example by using external magnets which create an external magnetic field.

In some embodiments, the local scan may include generating a conical magnetic driving force, which may initiate a conical motion pattern of the imaging capsule in the body lumen. For example, the conical magnetic driving force may be generated by generating a forward driving magnetic field and at least two orthogonal harmonic magnetic fields. In some embodiments, sensing pressure forces acting on the imaging capsule may include calculating the difference between an expected spatial positioning of the capsule as a result of the forces generated in the local scan motion and an actual spatial positioning of the capsule determined by a capsule positioning unit.

Relative position information of the imaging capsule in the three-dimensional operating space may be received, for example from fiduciary elements which may be positioned on the patient's body and/or on the operating table or bed on which the patient is lying during the imaging procedure. The rotation and translation of the imaging capsule may be calculated, for example based on the capsule positioning information received from the position/localization unit, and/or on the relative position information received from the fiduciary elements.

In some embodiments, when no target direction vector may be calculated using one or more methods, the external magnetic fields may be shut down or substantially lowered, in order to allow the capsule to naturally resume the correct direction and orientation for proceeding through the body lumen.

In some embodiments, if bubbles, particles, bile and/or turbid media are detected in an image captured by the imaging capsule, an obstruction level of the image may be calculated for that image. Images having an obstruction level that exceeds a predetermined threshold value may be ignored, removed or excluded from the calculation of the target direction vector.

According to embodiments of the invention, a system for automatically maneuvering an in vivo imaging capsule in a body lumen, may include, for example, an imaging capsule with an imager, a pressure sensor and a transmitter. The pressure sensor may produce pressure data representative of forces acting on the imaging capsule in vivo. The system may further include a receiver to receive in vivo image data, pressure data and other data which may be produced in the imaging capsule. A capsule positioning unit may indicate the current position of the imaging capsule within the three-dimensional space of the imaging system, and produce corresponding (current) position data. External magnets may be used to generate a driving force to navigate the imaging capsule according to a calculated target direction vector. The external magnets may also be used, for example, to locally scan the body lumen by the imaging capsule by causing a predetermined motion pattern of the imaging capsule within a region proximate to its current position. The system may include a processor to calculate a target direction vector for navigating the imaging capsule based on image processing, and/or based on the direction producing a minimal pressure force on the imaging capsule, which may have been sensed during the local scan.

According to some embodiments, the capsule positioning system may include internal coils in the imaging capsule, gravity sensors or accelerometers. The system may include fiduciary elements, which may be placed on or attached to the patient or on a fixed component or reference point in the system such as the operation table (e.g. the bed) on the floor, etc.

According to some embodiments, a method is provided for automatically navigating an in vivo imaging capsule in a body lumen of a patient. The method may include receiving, substantially in real time, an in vivo image of the body lumen captured by the imaging capsule, acquiring current position coordinates of the imaging capsule, and detecting a leading pattern in the received image. In some embodiments, if a leading pattern is detected, a center of the leading pattern may be calculated or estimated, either within the image or beyond the image boundaries. A target direction vector for propelling the imaging capsule may be determined based on center of the leading pattern.

In some embodiments, if a leading pattern is not detected, a local scanning motion of the imaging capsule may be initiated. The leading pattern may include a lumen hole or a wrinkle pattern.

In some embodiments, a system for automatically navigating an in vivo imaging capsule in a body lumen is provided, the system may include an imaging capsule comprising an imager and a transmitter, a receiver to receive in vivo image data from the imaging capsule, and a capsule positioning unit to indicate current position data of the imaging capsule. The system may also include a processor adapted to attempt to detect a leading pattern in a received image, find a center of the leading pattern and determine a target direction vector for propelling the imaging capsule based on center of the leading pattern. If a leading pattern is not detected, a local scanning motion of the imaging capsule may be initiated using the magnetic fields for maneuvering the capsule.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein:

FIG. 1 is a schematic illustration of an in-vivo imaging system, according to an example embodiment;

FIG. 7 illustrates the external magnetic maneuvering forces acting on the capsule according to an example embodiment;

FIG. 8A illustrates a capsule creating tissue drag in the intestine according to an example embodiment;

FIG. 8B illustrates a capsule propelled forward with superimposed conical motion according to an example embodiment.

Figure 2:
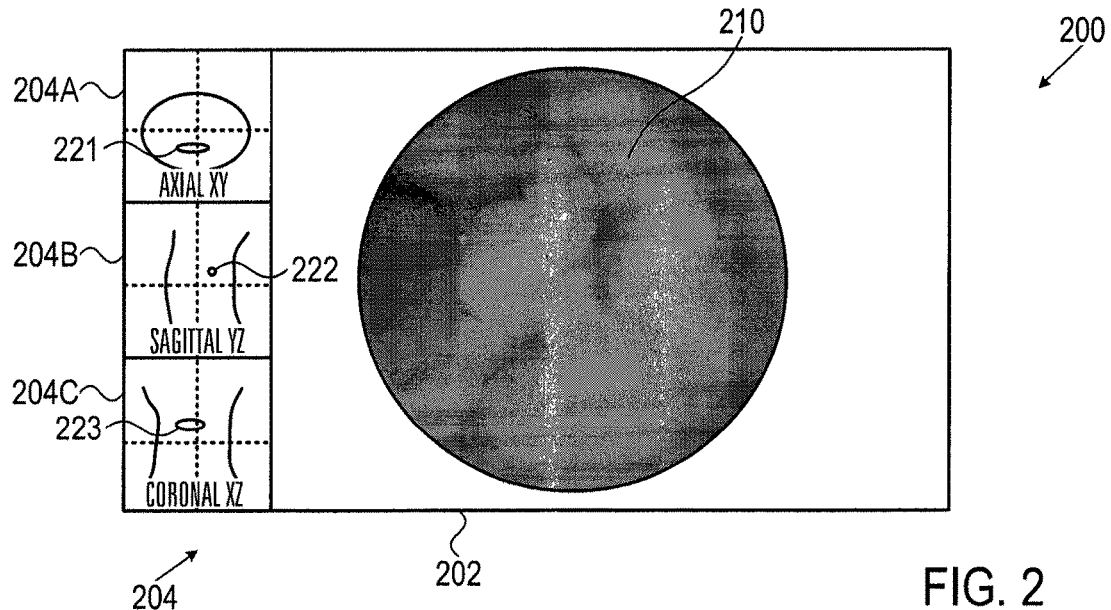
FIG. 2 illustrates a display for the use of a physician during navigation of a capsule endoscope according to an example embodiment.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise controllers, computers or processors selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include an article such as a non-transitory computer or processor readable medium, or a non-transitory computer or processor storage medium, such as for example a memory, a disk drive, or a USB flash memory, encoding, including or storing instructions, e.g., computer-executable instructions, which when executed by a processor or controller, carry out methods disclosed herein.

Some embodiments of the present invention are directed to a typically swallowable in-vivo device/capsule, such as an autonomous swallowable capsule. In other embodiments, the in-vivo device need not be swallowable or autonomous, and may have other shapes or configurations.

Reference is made to FIG. 1, which schematically illustrates an in-vivo magnetically guided capsule endoscope system 100 according to embodiments of the invention. According to some embodiments system 100 may comprise a capsule 40 having magnetic elements 48 or elements responsive to magnetic field, e.g. one permanent magnet or a set of permanent magnets or a combination of permanent magnets and metal discs or sheaths, a power receiving unit 49 and a capsule localization/positioning unit 43, which may include, e.g. coils, Hall Effect probes, gyro, acceleration meter, etc. Power receiving unit 49 may wirelessly receive power, for example, by 'picking up' electromagnetically energy. Capsule 40 may be surrounded by external magnetic field generators, e.g. coils 60. System 100 may comprise a patient diagnosis chamber 50, which may include an array of electromagnets (coils 62) arranged around a subject's torso on a standard patient table or carriages 54. Carriages 54 may be installed on rails located on or next to diagnosis chamber 50 and may slide in and out of diagnosis chamber 50. In some embodiments, carriages 54 may be fixed, and may enable diagnosis chamber 50 to slide along them. Diagnosis chamber 50 may also include an antenna or antenna array (antenna 52) to facilitate communication between capsule 40 and a data receiver 12, using a wireless communication such as radio frequency ("RF") communication, acoustic waves and/or ultrasound based communication. Antenna or antenna array 52 may be placed at various locations around chamber 50 or may be embedded within or below carriage 54.

Capsule 40 may be a swallowable in-vivo capsule, but other sorts of devices or suitable implementations may be used. In an example embodiment, capsule 40 may communicate with an external receiving and display system to provide display of data, control capability, or other functions. Power to capsule 40 may be provided, for example, by an internal battery, and/or by any device or circuit capable of picking up power, like coils responsive either to magnetic fields or to an RF transmission or any other wireless receiving system. Other embodiments may have other configurations and capabilities.

Capsule 40 may include an imager 46 for capturing images, an illumination source 42 for illuminating the body lumen, and an electronic circuitry and transmitter 41 to control the capsule functionalities such as transmitting image data and additional data to data receiver 12. Electronic circuitry and transmitter 41 may include, for example, an input-output ("I/O") interface/device, one or more controllers and a receiver. The receiver may be used, for example, to receive control information (e.g., to change a mode of operation, to change the value of a parameter, etc.), various messages. An optical system, including, for example, lenses or mirrors, may be used to focus reflected light onto imager 46.

Data receiver 12, preferably including a processor 16, may receive data from capsule 40. Processor 16 may be, for example, a DSP or any other real time processor or controller. In some embodiments, data receiver 12 may include a storage unit for storing the received data, while in other embodiments the data may not be stored in the receiver, and may either be transmitted or transferred to another storage unit or may not be stored at all. Processor 16 of data receiver 12 may calculate the localization parameters of capsule 40, and may be responsible for other communication tasks such as sending the data to a regulator of diagnosis chamber 50 and to the physician display station.

According to one embodiment of the invention, system 100 may include a control unit, which is referred to herein as a Medical Displays and Control Console (MDCC) (the MDCC is shown at 20), for receiving the stream of images and localization data from data receiver 12, processing the images' stream and localization data and displaying the stream of images (or individual images) and the localization data (and optionally additional information) to the physician. An input device 24 may be operationally connected to MDCC 20, and may be used to receive input of destination data for capsule 40 from a user (e.g., input device 24 may be or include a joystick, a pointing device or mouse, a keyboard, touch screen, stylus, light pen, trackball, or any other input device). The input data, or a modified or processed version thereof, may be sent to the regulator of diagnosis chamber 50 in order for it to facilitate generation of maneuvering commands. MDCC 20 may include a data processor 14, a storage unit 19 for storing, for example, data processed by data processor 14, and one or more monitors such as image monitor 18, which may be included as part of a personal computer or workstation which includes standard components such as a processor, a memory, a disk drive, and input-output devices, although alternate computer configurations are possible, and the system and method of the present invention may be implemented on various suitable computing systems.

Data processor 14 may include any standard data processor, such as a microprocessor, multiprocessor, accelerator board, or any other serial or parallel high performance data processor. Image monitor 18 may be a computer screen, a plurality of screens, conventional video displays, or any other device capable of providing a video stream, images and/or other data.

Preferably, imager 46 is a suitable complementary metal-oxide-semiconductor (CMOS) camera, such as a "camera on a chip" type CMOS imager specified by Given Imaging Ltd. of Israel and designed by Micron Technology, Inc. In alternate embodiments, imager 46 may be another device, for example, a charge-coupled device (CCD). Illumination source 42 may be on include, for example, one or more light emitting diodes, or another suitable light source.

In operation (during the imaging process), imager 46 may capture images and send data representing the images (e.g., image data) to transmitter 41. At the same time, localization unit 43 may detect signals representing location, and may output corresponding localization data to transmitter 41. Transmitter 41 transmits the image data and the localization data, or localization signals representing the localization data, to data receiver 12 using, for example, electromagnetic radio waves. Data receiver 12 may transfer the image data, and optionally other types of data, to data processor 14 that may store the transferred data in storage unit 19. In parallel, data receiver 12 may also transfer the data to the regulator of diagnosis chamber 50 to allow motion control of capsule 40. The data (e.g., image data and localization data) collected and stored may be stored indefinitely, transferred to other locations, or manipulated or analyzed. A healthcare professional may use the images to diagnose pathological conditions of, for example, the GI tract, and, in addition, the system may provide information about the location of these pathologies. The data may be analyzed and used as input for the maneuver control and analysis unit 28.

According to one embodiment, still images transmitted from capsule 40 as it traverses the GI tract may be combined consecutively to form a moving image stream and transmitted, sent or otherwise communicated to image monitor 18, which may either be connected to data processor 14 or remotely located in a central review station, where a healthcare professional may view the images as a live or real time movie.

According to embodiments of the invention, capsule 40 may be shaped in a cylindrical manner; in other embodiments it may have an egg shape, a ball shape or any other round-type shape with no sharp edges.

Data processor 14 may analyze and edit the data, storage unit 19 may store raw data and/or processed data, and may provide the analyzed and edited data to, for example, a healthcare professional at a later time.

Capsule 40 may record images at a rate of, for example, two to forty images per second, other rates may be used. Capsule 40 may have a fixed or variable frame capture rate and/or transmission rate, fixed or variable field of view, and fixed or variable image magnification which may be changed automatically or by a command from a user. When imager 46 has a variable or adaptive frame rate (AFR) capability, imager 46 may switch back and forth between frame rates, for example, based on parameters, such as capsule 40 speed, estimated location, similarity between consecutive images, or other criteria. The image recordation rate, the frame capture rate, the total number of images captured, the total number of images selected for the edited moving image, and the view time of the edited moving image, may each be fixed or varied.

Preferably, the image data recorded and transmitted by capsule 40 is digital color image data, although in alternate embodiments other image formats may be used. In an exemplary embodiment, each frame of image data includes 256 rows of 256 pixels each, and each pixel may have associated with it binary bytes for quantifying the pixel's color and brightness, according to known methods. Other numbers of pixels may be used, for example 320×320 pixels may be captured in an image frame, or high definition video resolution may be used, e.g. 1,280×720 pixels. For example, in each pixel, color may be represented by a mosaic of four sub-pixels, each sub-pixel corresponding to primary colors such as red, green, or blue (where one primary color is represented twice). In alternate embodiments, other formats such as hyper-spectral with multiple color filters may be used. The brightness of the overall pixel may be recorded by a one byte (i.e., 0-255) brightness value. According to one embodiment, images may be stored sequentially in data processor storage unit 19. The stored data may include one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

According to an embodiment of the invention, there is a maneuver regulator (e.g., maneuver control and analysis unit 28). Maneuvering regulator 28 may be a Programmable Logic Controller (PLC) or any other suitable commercial regulator known in the art. Maneuver control and analysis unit 28 may be a Modular PLC Controller which may include discreet input and output modules, a module for monitoring a cooling system, a thermocouple module for coil temperature monitoring, dedicated modules for power monitoring, etc.

Maneuvering regulator 28, an example maneuver control and analysis unit, may receive input data, such as localization information detected by localization unit 43, and commands from control console 30, and generate/output, based on the input data and using dedicated algorithms, electrical current commands for coils 60 for producing magnetic fields for driving capsule 40 within the GI tract.

Coils 60 may induce controlled and regulated magnetic fields, for example as per the electrical current commands output/generated by maneuvering regulator 28. The magnetic fields generated by coils 60 may interact with magnetic elements 48 to produce controlled translation and torque forces for moving, rotating and orienting capsule 40.

Moreover, the arrangement as described herein not only provides the forces and rotational torques to be exerted on the internal magnetic and conductive elements of a vessel such as the capsule to move, tilt and rotate in the body lumens, but also to follow, for example, an operator's or, automatic computer generated direction and orientation commands.

According to some embodiments, the external magnetic fields need to overcome a force in the range of, for example, 10 grams or 100 grams.

According to some embodiments, pressure sensors may be installed in guided imaging capsule endoscope, such as capsule 40, in order to provide information regarding the pressure that the capsule exerts on a wall of a body lumen. In an alternative or a complementary embodiment, measurement of the pressure exerted by the capsule on a tissue of a wall of a body lumen may be deducted from the movement of the capsule when the resistance to the movement (if the capsule is driven into the tissue) is detected by the location system. For example if a certain amount of force is expected to move the capsule two centimeters (cm) away but the capsule actually moved only 1 cm, it may indicate unexpected resistance and thus may be interpreted as a movement of the capsule into a lumen wall or as the movement having a vector component directed towards the lumen wall.

In one embodiment, one or more pressure sensors 44 may be positioned on the housing of capsule 40, for example creating a structure similar to a ring near the capsule dome. Pressure sensors 44 may be located on the front of capsule 40, or on another part of the capsule in order to detect occurrences of high pressure acting on the capsule 40 during the medical examination, and/or to detect peristaltic waves and provide input to maneuvering regulator 28 to increase counter forces to reduce such pressures. Such pressure sensors may be similar to, for example, General Electric's P161 sensor, which is a miniature silicon piezoresistive pressure sensor die.

According to a preferred embodiment, fiduciary elements 61 are attached to the subject to be examined, the subject lies on carriages 54 and his/her set of position coordinates relative to the bed is measured and used to calibrate the diagnosis chamber 50. Such setup/preparation procedure may take a short time, for example less than one minute. A capsule may be inserted into, or swallowed by the patient. The maneuvering magnetic fields are then activated and the capsule navigation may commence. A patient is expected to undergo the medical imaging procedure for a time period ranging from, for example, a few minutes for a short screening procedure (e.g. upper GI exam) up to two hours for a more lengthy GI tract examination. Typically, the system may work continuously during the day. Overlap may be possible, for example in the workstation level, for example during a current examination or imaging session, the results, or outcome, of a previous examination, or imaging session, may be handled (e.g., reviewed, further processed, stored or archived on the workstation or on another networked station).

According to embodiments of the present invention, a physician may view real-time movie images transmitted by the capsule endoscope in virtually real time, may watch the viewed organ or tissue concurrently from several perspectives, viewpoints and angles, and, optionally, use the visual feedback to navigate the capsule to a desired location, to position it in a desired orientation and to stop it—as may be needed.

To facilitate the capabilities described herein, MDCC 20 provides a live video display of the organ or tissue of interest, as received by the optical system of the capsule endoscope along with schematic representation of the location and orientation of the capsule, for example on the same display screen, employing side areas next to the display of the organ./tissue.

Reference is made now to FIG. 2, which illustrates a display 200 for the use of a physician during navigation of a capsule endoscope according to example embodiments. The display area of display 200 may be partitioned into multiple partitions or subareas. For example, a first subarea (e.g., subarea 202) may display an image (e.g., image 210) captured by the capsule endoscope camera or other sensing means, a second subarea (e.g., subarea 204) may schematically display the location and orientation information pertaining to the capsule at the time image 210 (to continue the example) was captured. A subarea may also be partitioned. For example, subarea 204 may be partitioned to subareas 204a, 204b and 204c, for displaying the location and/or orientation information pertaining to several points of view. Subarea 204a may display, for example, a schematic view of an axial (or transverse) plane of the patient's body, and may display an indication 221 of the current position of the capsule using (X, Y) coordinates of the capsule in the axial plane. Subarea 204b may display, for example, a schematic view of a sagittal plane of the patient's body, and may display an indication 222 of the current position of the capsule using (Y, Z) coordinates of the capsule in the sagittal plane. Similarly, subarea 204c may display, for example, a schematic view of a coronal plane of the patient's body, and may display an indication 223 of the current position of the capsule using (X, Z) coordinates in the coronal plane. Additional subareas may be used to present the trajectory of capsule 40, as well as various operational parameters, information or indicators required, for example, to monitor the current status or state of system 100, for example to monitor the intensity of the magnetic fields, electrical currents in the coils, temperature of cooling coils, etc.

According to some embodiments, the user (e.g. the physician) may control the capsule by selecting a direction for driving the capsule, and selecting the capsule's orientation. If an area of interest is detected in a particular image (e.g., in image 210), either automatically by image processing detectors or visually by the user, the user may mark the area of interest in the image and control the capsule to navigate or guide the capsule towards that area.

Figure 3A:
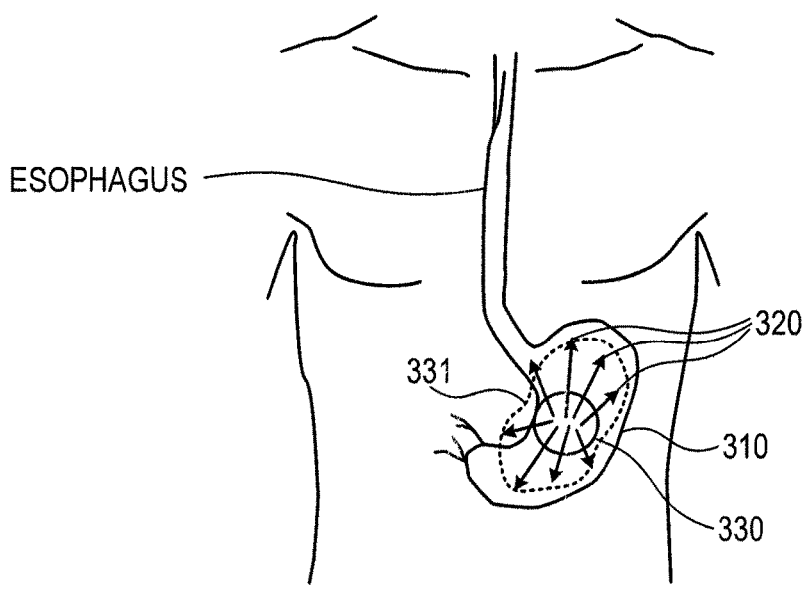
FIG. 3A shows a generic model of the stomach according to an example embodiment.

To ensure full visual coverage (e.g., complete imaging) of the tissue in a specific organ, and to detect abnormalities or aberrant geometry or shape in the imaged tissue, a generic model of the imaged organ may be estimated and constantly updated in real time, based on the location of the capsule. The positioning and orientation of the capsule may be determined based on localization unit 43. FIG. 3 shows an initial generic model 330 of the stomach 310. The initial model 330 may be generated automatically, based on a predetermined known or estimated structure of the imaged organ. In an example embodiment the user (e.g. physician) may guide or drive the capsule to the Gastro-Esophageal junction by using live video. When the capsule touches the Gastro-Esophageal junction, the physician may mark the location using an input device such as a joystick, mouse, keyboard, touch-screen or other input mechanism generally marked as device 24. The location marking command may initiate readout of localization unit 43. The data output by localization unit 43 may be translated into location data, and the capsule's position relative to fiduciary elements 61 and to the coordinates of carriage 54 may be determined. Based on live video images captured by capsule 40, the physician may navigate the capsule to a different landmark in the body lumen, e.g. to the pylorus, and mark its location in a similar way. Additional regions such as the top of the fundus zone, the cardiac notch, bottom of atrium and others may be marked similarly. The initial model 330 may be automatically updated, for example periodically, intermittently, or continuously, or may be updated upon user request, by setting the corresponding location in the model to reflect the actual size dimensions of the organ and the organ's location in the body. The initial model 330 can be improved by using a smoothing algorithm. The smoothing algorithm may perform a local polynomial (or other) regression on a series of location and orientation values and may determine the smoothed value for each point.

Once a personal or customized model 331 of the organ is estimated per patient, and based on the known imager/camera properties, for example field of view (FOV), the coverage of the organ by the imaging capsule may be calculated as the procedure proceeds. The coverage of the organ by the imaging capsule may include, for example, an indication of a percent or portion of the organ that was imaged during the procedure, at a certain point of time. For example, for every frame or for a subset of the frames in the image stream, the location and orientation data of capsule 40 may be transmitted, separately or together with the image data. Based on the customized model of the organ, the position of the capsule in relation to the organ tissue walls may be calculated, and thus a projection of the image on the model 331 may be estimated. Estimating the image projection on the model 331 enables verifying that the tissue walls of the organ under examination (stomach 310, for example, or another organ, e.g. the colon, small bowel, cecum, etc.) have been completely covered (imaged) during the imaging procedure, e.g. that the entire tissue of the organ has been imaged. In some embodiments, a three-dimensional visualization of the organ can be constructed from the images and displayed to the user.

In another embodiment, automated navigation may be based on a combination of predetermined motion pattern of capsule 40 and the ability of system 100 to automatically detect when capsule 40 is touching the tissue wall. For example, the control system, e.g. maneuvering regulator 28, may be set to move the capsule in a zigzag, somersault or rolling motion, changing direction whenever an indication that the capsule touches the organ walls is received. Such indication may be received, for example, from one or more pressure sensors which may be located on the capsule (e.g., pressure sensors 44), or by analysis of images, for example when the image intensity is very high (e.g., passes a predetermined threshold) it may be determined that the capsule is very close to the body lumen walls, or substantially touching the walls. The examined organ, e.g. stomach can be inflated by water or any other transparent liquid or gas. Once it is determined that the capsule is touching the lumen wall, location of the capsule may be measured using localization unit 43, and the model 330 may or may not be updated. A controller may automatically change the course of device 40, to ensure complete coverage by the imaging device.

In addition to pressure sensors, other methods can be used to automatically detect when the capsule is touching the organ wall. In some embodiments, the contact may be detected by measuring the intensity of the light reflected from the tissue. When the dome of the capsule is in contact or substantially in contact with the tissue, most of the illumination produced by the illumination units may be reflected back to the imager, and when the dome or a portion of it are not in contact with the tissue, a significant portion of the illumination may be scattered. Thus for a given camera, a threshold value of imager illumination intensity may be predetermined, and if the image or a portion of it reaches or exceeds the threshold value, it may be assumed, and therefore automatically determined, that the dome or a portion of it is touching the tissue. Another way to determined whether the capsule's dome is touching the organ wall involves measuring the location change between two consecutive localization measurements while the capsule is controllably moving e.g. straight forward. For example, while the driving controller is imposing magnetic forces on the capsule to drive it forward, a localization measurement may be taken at high frequency, e.g. 2-200 times per second. When consecutive measurements indicate that there is no motion of the capsule, it may be determined that the capsule reached the organ wall. The capsule may be automatically controlled to change its course, and the data (e.g., image data, localization data) obtained during the process may be used to update the organ model, and also to calculate a new course of motion for the capsule. The new course may be set by using a variety of scanning methods as described below.

In a preferred embodiment, the estimation of organ dimension, structure and 3D location, and orientation of the capsule may automatically be performed during the examination/imaging by extracting, or calculating, a distance vector from the tissue to the capsule by performing image analysis. The location of the viewed organ wall can thus be determined, and a 3-dimensional (3D) representation of the organ may be constructed and/or used for calculating the next target position of the capsule and/or the next movement direction/orientation of the capsule. According to some embodiments, the distance between the known location of the capsule and the location of the organ's wall may be estimated based on the illumination level of an image or a portion of an image, e.g. as described in U.S. patent application Ser. No. 11/907,550 to Krupnik et al., and/or in U.S. patent application Ser. No. 12/159,303 to Pascal et al., both assigned to the common assignee of the present application and incorporated herein by reference, or by using other methods as known in the art, for example illuminating structured or collimated light (e.g. grid) on the organ tissue, to extract 3D information of the organ. The structured light can be of different wavelengths, to reduce the burden of the software processing and create a "smooth" 3D surface.

Different types of scanning patterns may be used to cover the whole organ, such as moving the capsule in a zigzag motion or generating a spiral scanning movement of the capsule in the organ (e.g., a helical or twirling motion). In one example, the capsule may be driven along a straight line or curved line, for example touching the walls of the organ. In some embodiments, an external magnetic field may propel the capsule forward. An effective manner to drive a capsule may include a combination of a forward vector that may drive the capsule to a required direction and a twisting (e.g., screw-like) vector that may release the capsule from the encompassment of the surrounding tissue, in order to reduce resistance forces (e.g., drag, friction) between the capsule and the tissue walls. In a preferred embodiment, the scanning movement pattern of each organ may be different and adapted per type of organ, e.g. helical movement in the stomach, screw-like movement in the small bowel, and somersault movement (e.g. as disclosed in U.S. patent application Ser. No. 12/121,432) in the colon. Any other systematic navigation algorithm or a combination of different navigation and driving methods may be used.

For example, a method for ensuring image coverage of the stomach tissue may include generating a model 330 when capsule 40 is in stomach 310. The model 330 can be described as an arbitrary hollow geometric shell that represents the inner surface of the organ chamber with the capsule positioned substantially in the center of the shell. Initially, the envelope of initial model 330 may be created as a sphere or in a spherical or egg-like form, and may be sliced into a predetermined number of slices based on the known field of view (FOV) of the camera and optical system. In one embodiment, the capsule may be guided to move arbitrarily in a direction represented by a vector perpendicular to one of the slices, and stop moving if one of the two conditions occurs: (1) the output signal of some pixels of the imager indicate by using one of the methods described above, that the capsule contacts the organ's tissue, or (2) the average illumination reaches a threshold value representing good illumination and, therefore, good quality of image. At that point, the location of the organ wall may be estimated based on one of the methods described above. The capsule can then be moved back to its original location, and the next slice may be chosen. Imaging in all directions and ensuring coverage of the spherical model 330 enables verifying that substantially the entire stomach tissue was imaged.

Other capsule movement algorithms may be used. For example, at the first point/location of the capsule the capsule may be rotated around to visually scan all visible areas (all images or section of images reaching the threshold value regarded as good illumination), then the distance and location may be recorded for all scanned sections, then the capsule may be moved in a direction pointing towards the darkest while recoding all good images or section of images on the way. When a new location is reached by the capsule, the model (e.g., model 331) is re-established, knowing the coordinates of the first locating and the coordinates of the new location the model can be re-established and the viewed slices can be marked and the process may be repeated again, for example for addressing only unviewed slices. Direction arrows indicating the capsule movement may be added and/or displayed based on the positioning data received from the position sensing coils in capsule 40 (e.g., localization unit 43).

In some embodiments, other or different types of data may used—and the other or different data may be synchronized or tagged based on the time it was captured. A first type of data may be the position and orientation data of capsule 40, which may be derived based on the capsule's internal magnets, coils, or Hall probes, which may be part of, for example, localization unit 43, that sense the external magnetic field. This data may be provided with respect to one or more external reference points or coordinates, such as fiduciary element 61 which may be attached to diagnosis chamber 50 or directly to the patient. A second data type may include image data sensed by the capsule endoscope and transmitted by its transmitter. The visual data may be accorded to, or associated with, known locations within a body lumen, based on image processing techniques and/or the professional knowledge of a physician. The latter type of data is relative to locations in the body. A third type of data may include pressure measurements produced by pressure sensors 44 of capsule 40. In order to obtain an accurate reading of the capsule position and orientation in the body lumen, it may be required to combine, use, or synchronizing between the two or more different data types.

After, or while, position/orientation information is collected by the capsule, the information may be transmitted concurrently or simultaneously with image data, for example by using the same frame, or separately, for example by using different frequencies, or by using sidebands of a basic transmitter. If more than one transmitter are used (e.g., one transmitter for transmitting image data and another transmitter for transmitting position/orientation information), the transmitters may be operated by either using a common clock or separate/independent clocks.

According to embodiments of the present invention, a capsule endoscope may be automatically navigated in the body lumen. According an embodiment the automatic navigation mode may be tuned or configured to guide the capsule from a current, temporary location, towards a center of a lumen hole identified in the images.

Figure 3B:
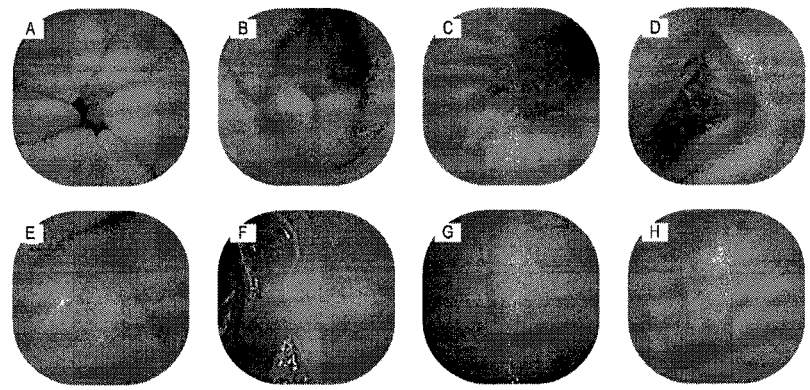
FIG. 3B shows eight sample images (designated as A, B, . . . , H) taken within a body lumen according to an example embodiment.

Reference is made to FIG. 3B, which presents eight sample images A, B, C, D, E, F, H taken within a body lumen, with different angles of view of the lumen walls (e.g., different angle of orientation of the capsule 40 during the capturing of each image). Sample images A-D present images were captured while the longitudinal optical axis of the capsule 40 was parallel to, or directed substantially towards, a lumen hole or lumen opening. A lumen hole may be clearly seen in these images as a darker portion of the image. Sample images E-H were captured when the longitudinal optical axis pointed away from the lumen hole, e.g., to the lumen's tissue wall.

Certain landmarks may be detected automatically, for example by processing the acquired images, or may be marked by the physician viewing the images during the medical examination procedure. According to some embodiments, a physician operating a MGCE (Magnetically Guided Capsule Endoscope) system may mark points of interest during exploration or scanning of a body lumen. The marked points may indicate or represent, or be associated with, universally known landmarks in the body lumen, such as the Z-line, pylorous, duodenum, splenic flexure, hepatic flexure, cecum or others. When maneuvering the capsule in the stomach for example, the physician may mark the entrance to the stomach (Z-line) and/or the stomach's exit (pylorous). A stomach model may be displayed on the monitor once the physician marks the entrance to the stomach or other landmarks in the gastrointestinal tract. The size and location of the model organ may be updated based on the position and orientation coordinates of capsule 40 (received from the magnetic positioning system) during capturing of the landmark image.

Figure 4:
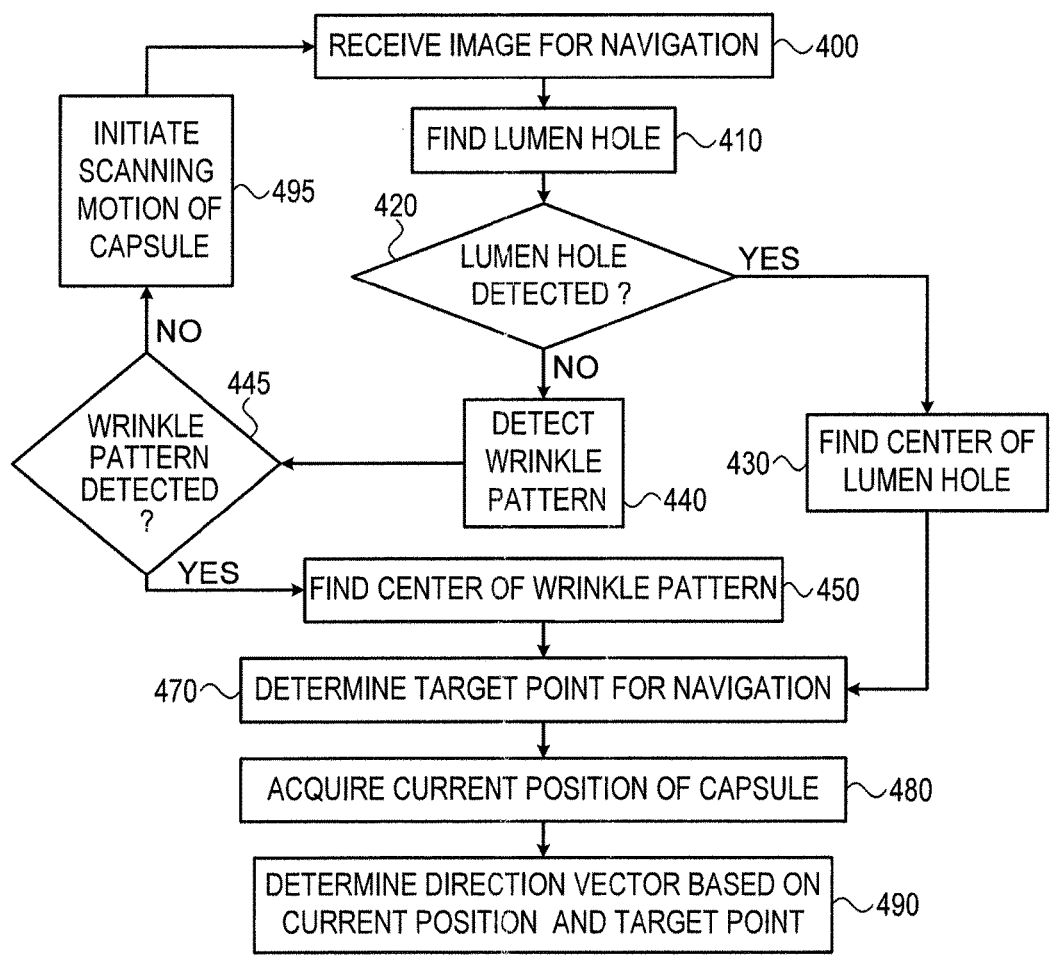
FIG. 4 is a flow chart of a method for automatic navigation of an in vivo imaging capsule based on images according to an embodiment of the present invention.

Reference is now made to FIG. 4, which is a flow chart of a method for automatic navigation of a capsule in vivo based on captured images according to an embodiment of the present invention. In operation 400, an image for navigation is received. The image may be captured by the in vivo imaging capsule 40, and may be received, for example in real time or substantially in real time (e.g., with minimal delay between time of capturing of the image by the imaging device and the time of reception of the image, by a receiving unit (e.g. data receiver 12). The receiving unit may be operationally connected to a processing unit (e.g. data processor 14 or another data processor) for determining a target vector for navigation of the capsule.

The automatic navigation of the capsule may generally follow the direction of the lumen hole, for example in the small intestine or in the colon. In operation 410, the processing unit may analyze the received image, for example to detect a lumen hole which may be depicted in the image. Methods for identifying a lumen hole within a series of image frames taken inside the lumen are disclosed, for example, in U.S. patent application Ser. No. 12/304,526 to Malagelada et al.

Every detectable pattern in an image (e.g., lumen hole, a central point of a star wrinkle pattern, etc.), which can be used to determine the center of the contraction, and from the center of the contraction a direction vector for moving the capsule, is referred to herein as a "leading pattern". Leading patterns other than lumen hole and wrinkles may be used to obtain a direction vector.

Figures 5A, 5B:
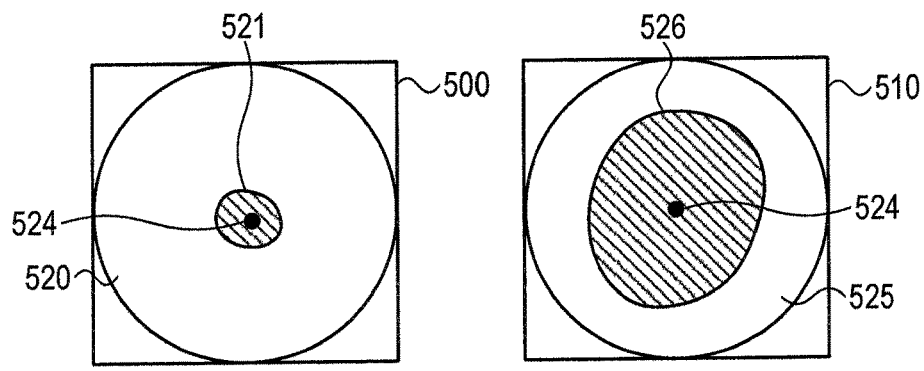
FIGS. 5A and 5B schematically present two images of the small intestine, with contraction and without contraction, according to an example embodiment.

Reference is now made to FIGS. 5A and 5B, which schematically present two images 500 and 510 of the small intestine. The images illustrate lumen walls and a detected lumen hole. In some embodiments, in the absence of contractions or during a period of relatively low or weak contractile activity, an outer portion (e.g., a ring-shaped portion 520 in FIG. 5A or 525 in FIG. 5B) of the captured in-vivo images may be relatively bright due to reflection of light from portions of the image corresponding to body lumen walls; whereas the inner portion corresponding to the lumen hole (e.g., a substantially central portion 521 in FIG. 5A or 526 in FIG. 5B) of the in-vivo images may be relatively dark (e.g., darker than outer portions 520, 525). An intestinal contraction, as demonstrated in FIG. 5A, may cause the body lumen to contract, such that the lumen walls may collapse and/or narrow on the capsule. As a result, in-vivo images acquired during a contraction period may be relatively bright, or may include a relatively larger bright portion 520 corresponding to the lumen walls, and a relatively small dark portion 521 corresponding to the lumen hole (e.g. relative to bright portion 525). Additionally or alternatively, in-vivo images acquired during a contraction period may not include a dark portion, or may include only a relatively small dark portion.

Referring back to FIG. 4, in operation 420 a processor may determine whether a lumen hole was detected. If yes, the center of mass of the lumen hole in the image may be calculated or estimated in operation 430. The center of mass 524 of the lumen hole in the image may be calculated based on the size of/and area of the dark portion within the image (corresponding to the lumen hole) to determine the direction at which the capsule should be moved, by calculating, for example in real time, the position or coordinates of the average weight of dark portions in the image, e.g. 520, 525. A dark or darker portion of the image may be given a larger weight, according to the intensity value of the pixel in the original image.

Other methods for detecting a lumen hole portion in the images may be used. The image may be segmented, for example using the Watershed algorithm, followed by selection of the darkest region, and calculation of the weighted average of the darkest region. Another method may include calculating the histogram of the image and setting an adaptive threshold of the dark region based on the separation of the regions in the histogram. In other embodiments the threshold may be set to a specific value, and not calculated based on the image gray-level parameters. In a preliminary step, the image may be blurred in order to remove small objects such as blood vessels or turbid particles in the image, and the darkest area of the image detected after the blurring process, for example an area in which the intensity value of a substantial amount of pixels is below a predetermined threshold, may be determined as the lumen hole.

In some cases no dark lumen hole may appear in some of the images. For example, in case of an occlusive contraction, a lumen hole may not appear. In other cases, the lumen hole may be outside the boundaries of the image (e.g. only tissue walls are visible in the image) or may not be visible due to turbid media which may be present in the body lumen and may obstruct the view of dark portion.

If no lumen hole is identified in the image, wrinkle patterns in the image may be detected in operation 440. A method for detection of wrinkle patterns, for example star wrinkle patterns in an in vivo image, and detection of the center of the wrinkle patterns (by detection of the star wrinkle pattern skeleton), is described for example in U.S. patent application Ser. No. 12/282,704 to Malagelada et al. A convergence of ridge lines of the star wrinkle pattern or a center of the wrinkle pattern, may indicate the lumen hole or the direction of the lumen hole, towards which the capsule should be maneuvered.

Analysis of a star pattern of the wrinkles (e.g. the ridge lines of the wrinkled tissue) in the image may be performed. If a wrinkle pattern is detected (operation 445), a center of a wrinkle pattern in the image may be determined in operation 450. For example, FIGS. 6A-6D, depict extraction of ridge lines in an image with a star wrinkle pattern. A center of a contraction may be detected by extracting the ridge lines 610 (in FIG. 6D) of the wrinkle pattern. The center 600 of the wrinkle pattern may be determined as the center of the contraction, which may also have a high correlation to the center of the lumen hole. In operation 470, the central point 600 of the leading pattern in the image may be translated to spatial coordinates in the living body lumen, and may be set as a target point for further navigation of the capsule.

In some cases, the capsule may capture images which include wrinkle patterns that may indicate a contraction of the intestine. However, the capsule endoscope may capture the contraction only partially, and the center of the contraction may remain out of view in the image, or may be hidden or obscured in the image (e.g. by turbid media which may be present in the intestines). In such cases, the center of the contraction may be estimated, extrapolated or inferred as an intersection or convergence point of the wrinkle skeleton lines. The direction of movement of the capsule may be set to the direction of the center of the contraction (even if it is outside the borders of the current image).

In some embodiments, the contours or ridges of the tissue walls may be detected based on the illumination level of the pixels in the image. Contours of the tissue may indicate the direction of the lumen. In one example, several substantially elliptical forms may be detected as the lumen tunnel, and the center of the each elliptical form may indicate the direction of the lumen opening. In another example, partial arcs may be detected. The order of occlusion of the arcs may be calculated, and may provide indication of the distance of the arc from the imaging device or from the capsule 40. The farthest arc detected may indicate the direction of the lumen opening.

Figures 6A, 6B:
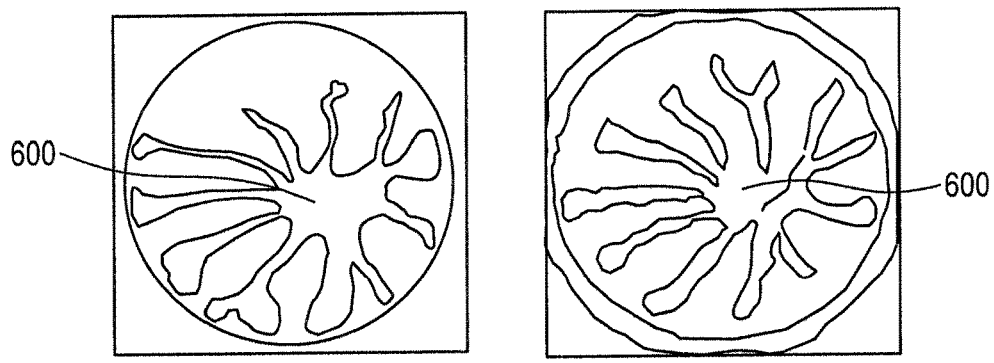
FIGS. 6A-6E schematically present images of the small intestine which show the wrinkles direction according to an example embodiment.
Figures 6C, 6D:
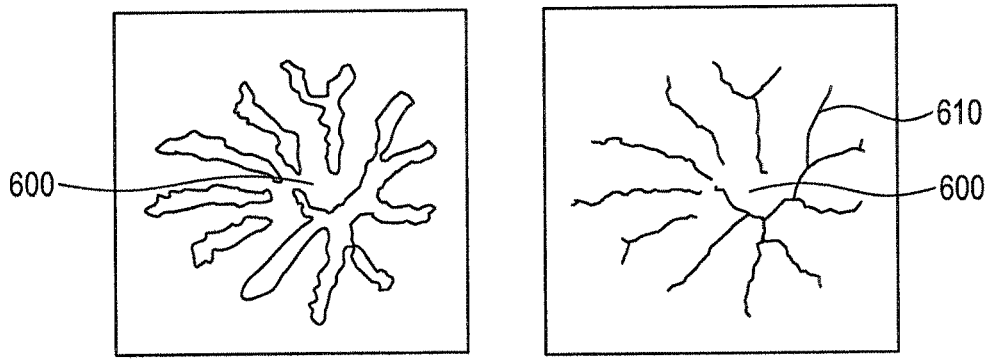
Figure 6E:
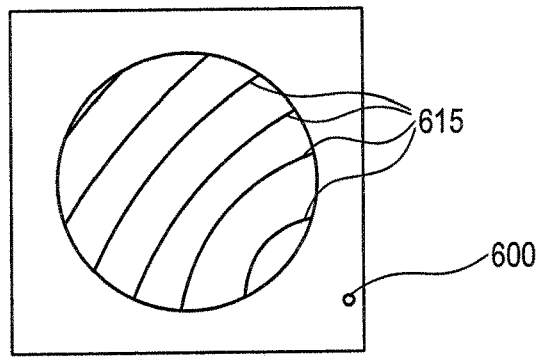

Reference is now made to FIG. 6E, which schematically illustrates a body lumen with tissue walls depicted as ridge lines 615. The lumen hole is not visible in this image, however, based on the leading pattern of the ridge lines 615, the center of the lumen hole may be estimated as point 600 of FIG. 6E, which is outside the boundaries of the captured image. Other methods for detecting wrinkle patterns or leading patterns in the lumen and calculating the center of the leading patterns may be used.

Referring back to FIG. 4, once the center of a leading pattern (e.g. lumen hole, wrinkle pattern or other pattern) is detected, estimated or extrapolated, it may be determined, in operation 470, as a target point in the image for maneuvering the capsule. The target point in the image may be translated to three-dimensional coordinates of the patient's body, e.g. based on current capsule position/location information, relative to the fiduciary elements 61 located on the carriage 54, or based on other position sensors which may be used. For example, the target point in the image may be converted to spatial coordinates in the patient's body, by estimating a distance of the target point in the image from the imager (or from the capsule). Estimation of distances of objects from the imaging device in an image captured in vivo may be, for example, according to the method disclosed in US Patent Application Publication No. 2009-0097725, assigned to the common assignee of the present application.

In some embodiments, the target point in the image may be translated to an actual point in the three-dimensional space of the body for maneuvering the capsule in the body lumen. Knowing the optical properties of the imaging capsule, each pixel in an image may be mapped to a ray of light in the three-dimensional space. The ray of light may start at the imager (or more specifically, at the specific light sensor of the imager which produced the image pixel), and pass through the optic focal point of the capsule's optical system, to a certain direction vector in the three-dimensional space. The distance of the image pixel from the capsule may or may not be known (or estimated). However, the mapped direction vector may be sufficient for navigation of the capsule in the determined direction. The optical model or map of the direction vector corresponding to each pixel in the imager may be calculated once, for example during manufacture or calibration of the imaging capsule. In some embodiments, a single direction map may be calculated per capsule and stored, for example in a capsule's internal memory.

In operation 480, a current spatial position of the capsule in the patient's body may be received or acquired, for example, through position/location data sensed or received by localization unit 43. Based on the current position coordinates and the obtained target coordinates, a direction vector may be calculated in operation 490. In some embodiments, the direction vector may include only a direction for maneuvering the capsule. In other embodiments, the distance to the target position may also be estimated, and the direction vector may comprise the spatial direction and actual distance for driving the capsule to a target location, or for a next maneuver of the capsule.

When navigating the capsule endoscope, some images may include turbid media, bile, particles or bubbles which may interfere with the detection of the lumen opening. In one embodiment, the processor may detect images which include turbid media, bile, particles or bubbles, and calculate a score or measure of the obstruction of the image caused as a result of the turbidity, for example by calculating the percentage of turbid media or particles that obstruct the tissue view. A threshold of obstruction may be determined, and images which include turbidity that passes the threshold of obstruction may be removed or ignored, in order to prevent calculation of an incorrect direction vector.

Images received for navigation may be analyzed to determine if they contain leading patterns. In some cases, a lumen hole may not be detected in an image or a sequence of images, and star wrinkle patterns or ridge lines (allowing estimation of a lumen hole direction) may not be detected either. This may be due to several causes: for example, some images may include turbid content, bile and/or bubbles, which may block or obstruct the view either partially or wholly. In other images, the optical system may be focused on the tissue walls and a lumen opening may not be visible in the image. In such cases, the magnetic maneuvering force may be deactivated, for example shut off or minimized to a low intensity, in order to allow the capsule endoscope to progress naturally (e.g., only by the peristaltic movements of the intestine) along the lumen, or to become oriented in the correct direction of the lumen for forward movement. Such deactivation of the magnetic maneuvering field may be useful especially in the small bowel, which has a relatively narrow tubular structure (compared to, for example, the colon or the stomach).

In wider or larger organs, such as the colon or stomach, when the capsule captures images of a tissue wall and no leading patterns are detected in the images, a scanning motion of the capsule may be initiated in operation 495, to attempt to detect a leading pattern, e.g. a lumen hole or a wrinkle pattern. The scanning motion may include, for example, a spiral, helical or conical movement of the capsule may be initiated by the magnetic activation force, until the image captured by the capsule shows a detectable lumen hole or contraction wrinkles from which the lumen opening direction may be deduced. The spiral movement may start out in a small diameter and gradually increase the diameter of the circular movement. This method provides automated/semi-automated means for advancing the capsule endoscope through a body lumen during a medical examination procedure. An exemplary scanning motion may be similar to a superimposed conical motion which is described in FIG. 8B hereinbelow.

Wrinkle patterns or wall structure of the colon may be detected automatically by pattern recognition, since these wrinkles are typically different than wrinkles that appear in the small bowel. For example, the wrinkles of the tissue walls in the transverse colon may have a typical triangular structure which may be detected automatically, and/or may be marked by the physician.

In some embodiments, the magnetic maneuvering force may be intermittent, e.g. activated on and off in pulses for short periods of time. The periods of time may be predetermined, and may be set for example by the user through a control unit of the magnetic maneuvering force. Such pauses in the magnetic field activation may allow the capsule to return to its natural orientation along the gastrointestinal tract. In addition or instead, the magnetic maneuvering force may be activated according to analysis of the imaging procedure, for example every frame or predetermined number of frames captured by the capsule, a new direction vector may be calculated and the maneuvering force may be generated accordingly.

Shutting off or lowering the magnetic maneuvering force may also be used as a safety element in the magnetic maneuvering system. In one embodiment, the magnetic force operating on the capsule may be determined and/or measured. The capsule may include one or more pressure sensors 44 located on or surrounding the external housing of the capsule. Pressure sensors 44 may provide indication of the pressure force which is exerted on the capsule. The pressure sensors 44 may be positioned, in one example, as a radial ring along the circumference of the capsule housing. In another example, several sensors may not necessarily be aligned on the external surface of the capsule. The signals sensed by the pressure sensors may indicate the direction from which the pressure originates. In some embodiments, the capsule may be propelled in a direction which is the opposite the pressure force origin. For example, when the capsule is maneuvered into a tissue wall, pressure sensors 44 may indicate that the pressure on the capsule exceeds a predetermined safety threshold, which may be dangerous for the patient (e.g., may cause rupture of the intestinal walls). In such cases, the magnetic maneuvering force may be automatically shut off or lowered, for example to a minimal intensity, thus preventing accidental damage to the tissue walls. Similarly, upon signals from pressure sensors 44 that indicate the amount of pressure acting on the capsule exceeds a threshold, the controller may automatically change or recalculate the next direction vector for propelling the capsule.

In one embodiment, control of the capsule maneuvering may be performed remotely. A nurse or other health care professional may set up the patient in the room with the magnetic maneuvering system, while the physician may not be present in the room, and may access the navigation control remotely.

In one embodiment, the total force acting on the imaging capsule may be determined and/or measured. For example, the pressure sensors 44 may provide indication of the total forces (e.g., pressure and magnetic forces) which are acting on the capsule. When the capsule is maneuvered into a tissue wall, the pressure sensors 44 may indicate that the pressure on the capsule exceeds a safety threshold, and may be dangerous for the patient (e.g., may cause rupture of the intestinal walls). In such cases, the magnetic maneuvering force may be automatically shut off or lowered, for example to a minimal intensity, thus preventing accidental damage to the tissue walls. In one embodiment, the signals from pressure sensors may be received by a receiving system, and a controller or processor may determine that the amount of pressure acting on the capsule housing exceeds a certain threshold. As a result, the controller may automatically change or recalculate the direction for maneuvering the capsule.

In some embodiments, the magnetic maneuvering force may induce enough force to progress the capsule forward in the intestine for a calculated distance. The difference between the expected movement of the capsule (e.g., as calculated by the controller) and the actual movement (e.g., the new position of the capsule determined according to the signals of the positioning component) may be calculated. If the localization unit determines that the capsule did not move a sufficient distance, or if the pressure sensors determine that the pressure on the capsule is too strong, the external maneuvering force may be stopped, or the direction/distance movement vector may be recalculated according to updated data received. For example, the magnetic maneuvering force may be operated to propel the capsule for a distance of 1.0 centimeter, but the position sensors may indicate that the capsule actually moved only 0.5 centimeter as a result of the driving force. In one example, the pressure sensors 44 may indicate that the pressure on a portion of the capsule exceeds a safety threshold while in other examples the position and orientation of the capsule in relation to its expected position may be calculated and analyzed. These two methods may be used separately or in combination, and the maneuvering forces may be stopped and re-calculated based on more recently captured pressure/position/image data.

In another embodiment, the capsule may be directed by the magnetic maneuvering force along the intestinal walls, for example, such that the capsule's housing is always touching the tissue. To increase the field of view of the capsule, the longitudinal axis of the capsule may be positioned in parallel to the progress direction of the capsule, and the optical system may be positioned in a forward-looking direction (e.g., towards the lumen hole and not toward the tissue walls).

In some embodiments, based on input provided by the capsule positioning coils, image data, and/or pressure sensors, it may be determined that a previously calculated target direction vector is incorrect or hazardous for the patient, and an alternative target direction for maneuvering the capsule may be calculated. In another example, a target direction vector for maneuvering the capsule may not be derivable from the image data transmitted by the capsule (e.g., no lumen opening is visible in the images, and/or the direction of contours of the tissue wrinkles is undetermined). An alternative target direction vector for maneuvering the capsule may be calculated, according to one embodiment, by determining the least amount of resistance force exerted on the imaging capsule by the surrounding tissue walls.

In order to find out the direction for propelling the capsule which will exert the least resistance force on the capsule, in one embodiment, a local scan or local scanning motion of the tissue area may be initiated, for example by generating a specific motion pattern of the capsule around its current spatial coordinates. The local scan movement performed by the capsule may cover the vicinity or surrounding area of the capsule's position. At certain points along the scan (e.g., based on the degrees of movement of the capsule orientation, or at predetermined time intervals during the scan) new pressure data indicating the forces acting on the capsule and/or new image data may be transmitted from the capsule. Based on the data obtained during the local scan, an alternative target direction vector for maneuvering the capsule may be determined. In one embodiment, the target direction vector may be selected according to the direction in which a minimal amount of pressure or resistance force acting on the capsule was detected. In some embodiments, image processing of the image data transmitted during the local scan may be performed, and the target direction vector may be determined based on the direction of the detected lumen opening, or based on the estimated direction of the lumen opening according to the wrinkle pattern in the images. If the images do not provide sufficient information for determining the target direction vector, the data provided by the pressure sensors may be used as described above.

In FIG. 7, the external magnetic forces acting on the capsule are shown. A forward driving force V(t) causes the capsule to progress forward in the direction of the opening of the body lumen. The desired direction and length or distance of V(t) may be determined automatically, for example using one or more of the methods described above, e.g. determining the central point of the dark portion in the image, determining the direction of the wrinkles of the tissue walls, and/or by calculating the minimal pressure/resistance of the tissue walls according to pressure sensor readings. The orthogonal driving vectors $V_h$, $V_v$ may be determined in relation to V(t), by selecting two mutually orthogonal vectors which are also orthogonal to V(t), in a vertical and horizontal orientation.

In one example, movement generated during the local scan may induce a conical motion pattern of the capsule. The generated movement may be induced by the external magnetic maneuvering forces, as shown in FIG. 7. In addition to generating a forward driving force in the direction of the target direction vector, the conical movement pattern may be simultaneously generated by applying a set of two orthogonal harmonic magnetic field vectors in addition to the forward driving field vector V(t). Typically, the orthogonal harmonic magnetic field vectors $V_h$, $V_v$ creating the conical motion are weaker than the forward driving field force V(t). In one embodiment, the orthogonal magnetic fields may be calculated according to the following equations:

$$V_h = A \sin \omega t$$

$$V_v = A \cos \omega t$$

A conical motion may be generated thereby, similar to known gyro mechanisms.

Due to the flexible and elastic attributes of the intestinal in vivo tissue, propelling the capsule forward in the direction of the calculated or provided target direction vector may create substantial tissue drag, which may prevent or thwart the capsule from progressing, or significantly slow its advancement in the lumen. For example, as shown in FIG. 8A, the capsule may be pushed forward by the external magnetic force, however the intestinal tissue walls may be collapsed around the capsule in a manner that causes dragging of the tissue instead of progression of the capsule through the lumen. Conical movement as shown in FIG. 8B may also be useful for generating effective forward movement of the capsule and reducing tissue drag. The conical movement may cause the collapsed tissue walls to separate, reducing the tissue encompassment of the capsule and thereby allowing forward progression of the capsule through the lumen opening, rather than tugging the tissue along with the capsule during the motion. Other types of motion patterns may be induced, for example a screw-like movement in which the screw is advanced in a single direction or in a back and forth manner, a pattern which includes partial twists or turns of the capsule's orientation in a predetermined amount of degrees, etc.

The progress direction of the capsule may be determined based on localization of the capsule relative to the patient's body. The patient may have an external localization unit, for example a permanent magnet or coils which can be localized by the magnetic system, may be positioned on the body of the patient. The capsule may have one or more internal positioning components such as internal magnets, coils or Hall sensors which may provide momentary position data of the capsule's movements. A relative movement path may be calculated, for example by subtracting the patient's body movements (e.g. breathing and heartbeat movements) from the capsule's position, to improve accuracy of the position data and movement data of the capsule in the body lumen. In some embodiments, pressure sensors 44 on the capsule may determine the direction of a peristaltic wave and identify the direction of movement accordingly.

The progress direction of the capsule may be calculated based on determining differences between sequential images. In one example, the progress direction of the capsule may be determined by identifying the direction of movement of tissue between one image frame and the next. In another example, the progress direction may be determined by identifying the direction of inclination or swaying of in vivo structures, e.g. villi in the small bowel, in sequential images. In yet another example, the progress direction of the capsule may be determined based on movement of content or residue in the body lumen. The residue or turbid particles may move forward relative to the capsule's movement, indicating that the capsule may be moving backward or stuck in place. When the capsule is progressing forward, the movement of the residue will appear backward. In some embodiments, the capsule may include a storage unit with colored (and non-toxic, edible) ink, and when the physician wishes to verify the relative movement of the capsule, a command may be sent from the controller to the capsule to release a drop of the ink, and the direction of flow will be visible in the captured images sent from the capsule, allowing determination of the progress direction based on automatic image processing or by the physician.

If it is detected that the capsule is progressing backwards instead of forward in the intestine, a somersault movement may be initiated, for example a command may be sent from an external control unit to the capsule, in order to flip the capsule to a correct orientation. The somersault movement may be similar to embodiments described, for example, in U.S. patent application Ser. No. 12/121,432.

To assist the physician in maneuvering the capsule, the capsule's path may be displayed constantly, on a monitor or screen which may be connected to a workstation. For example, the last few centimeters (e.g., 10 cm) that the capsule travelled may be displayed to the user in relation to the capsule's current location. Similarly, the display may include the last few minutes of the capsule's path or the path passed since a certain landmark image was marked.

In one embodiment, the direction of the gravity force may be detected, for example by adding a gravitation sensor to the capsule, and the generated display may be aligned with the direction of gravity in order to present to the physician a fixed viewing orientation of the lumen. In another embodiment, the capsule's orientation and position may be provided (or calculated) based on the signals from the position sensors, so no gravity sensors may be required in order to align the images to a single viewing orientation.

Thumbnails of marked images may be stored along with their spatial coordinate location. If the physician wishes to direct the capsule to a known position, for example to the spatial coordinates of the last captured thumbnail, the MGCE system may allow inputting specific coordinates or a specific landmark image, and may automatically navigate the capsule back to the required location. A display of the correct direction for maneuvering the capsule may also be provided upon request, for example an arrow pointing to the direction of the requested thumbnail may be displayed relative to the current capsule position.

For each frame captured by the capsule, a corresponding orientation and three-dimensional position of the capsule may be obtained (e.g., from the magnetic field sensors, position/localization sensors such as Hall probes or other positioning sensors) and stored. A visual model of the immediate space around the capsule (e.g., the surrounding area of 3 centimeters) may be generated and presented to the physician maneuvering the capsule. For example, the images captured in the surrounding area may be presented individually or stitched together and combined to a single panoramic image.

In some embodiments, not all images captured by the capsule may be presented to the user. For example, images which are captured when the imaging system is close to and pointed at the tissue wall, may be automatically removed or filtered out, and in one embodiment only images showing a view of the lumen hole, e.g. tunnel images or contraction images, may be displayed. Such filtering may assist the physician in maneuvering the capsule, since images which are not beneficial for providing maneuvering information may be removed from the stream or from display. The type of images shown to the physician may be selected or preset by the physician according to personal preference.

One or more external elements may be used as reference points and assist in calculating the accurate movement of the capsule in the body lumen. External elements 61 functioning as fiduciary elements 61 may be made of coils, for example, and may be connected by a wired or wireless connection to the workstation, for use as a point of reference in the system. Each fiduciary element 61 may produce a signal which may be processed in the workstation to determine the relative position of the capsule in the three-dimensional space, in relation to the fiduciary elements 61. The fiduciary elements 61 may be placed on the patient's body, for example external to the patient, and/or on the operation table or bed 50 on which the patient is lying. In some embodiments, the fiduciary elements 61 may include wireless units which may constantly or repeatedly transmit positioning or location information, as part of the MGCE system. In some embodiments, the fiduciary elements 61 may include wired units which may be operationally connected to, for example, the workstation or a controller of the external magnetic field. The positioning information produced by the fiduciary elements 61 may be used to calculate the relative and/or absolute movement of the capsule in the body lumen, for example by subtracting the patient's movements (e.g. caused due to breathing, voluntary movement, heartbeat, etc.) from the absolute capsule movement.

The fiduciary elements 61 may define a set of coordinates relative to the patient's body, and the capsule's location may be calculated in relation to this set of coordinates. The origin of the set of coordinates may be determined to be a fixed point, for example on the bed and not on the patient, in order to calculate the capsule's location in space relative to the fixed point. The calculated location of the capsule may be corrected, for example in real time, by subtracting the patient's movements (calculated according to the fiduciary elements 61) from the capsule's movements or path.

In some embodiments, the fiduciary elements 61 may be positioned in specific predetermined anatomical placements, such as substantially adjacent to the xiphoid process on the lower part of the sternum, or adjacent to the navel, in order to help locate an area which requires treatment. Positioning the fiduciary elements in predetermined placements on the patient's body may allow determining a location of a pathology (e.g. a lesion, a polyp, a tumor, bleeding, etc.) in a coordinate system which is aligned with the patient's skeletal structure.

Figure 9:
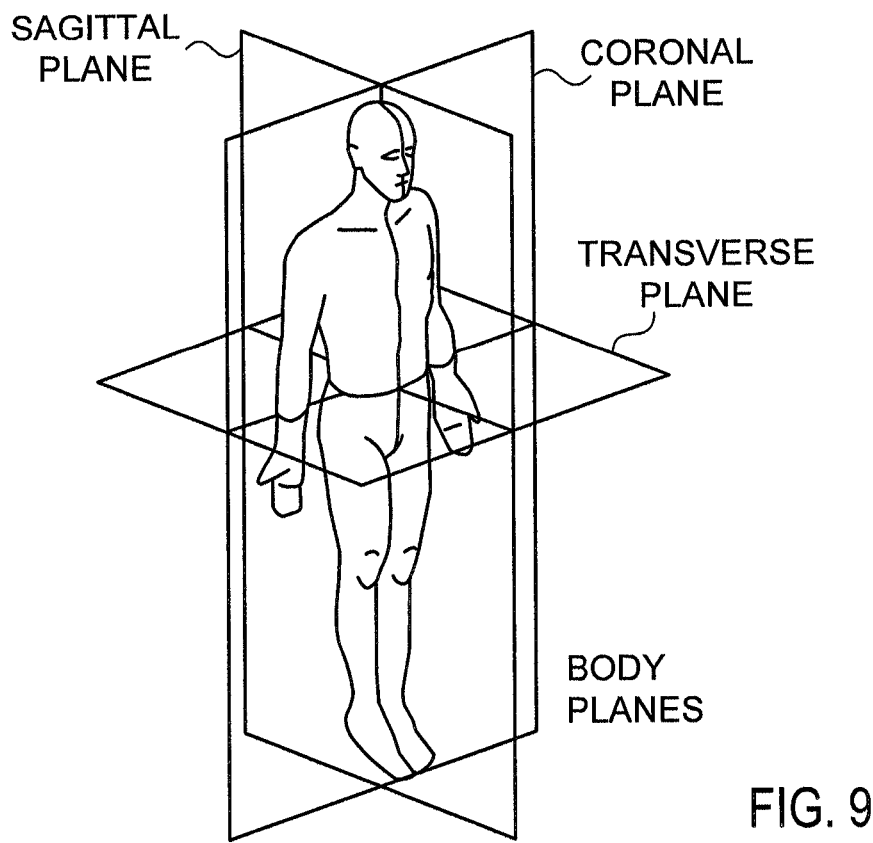
FIG. 9 illustrates a coordinate system of body planes according to an example embodiment.

In some embodiments, the set of coordinates used to determine the capsule's position may be defined in relation to the patient's body. For example, the physician may be interested to know the position of the capsule in relation to the patient's coronal plane, saggital plane, and/or transverse plane (shown in FIG. 9), regardless of whether the patient is lying on his/her side, back or stomach, and not necessarily in relation to the bed. In other embodiments, several planes or sets of coordinates may be defined, and the physician may choose a preferred plane or set of coordinates to work with, or may switch between different planes/coordinates in different stages of the medical examination.

It is noted that while embodiments of the invention described herein are adapted for imaging of the GI tract, the devices and methods disclosed herein may be adapted for imaging other body cavities or spaces.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for automatic generation of a model of an organ, the organ imaged by an in vivo capsule comprising an imager, the method comprising:
   capturing, via the in vivo capsule, light-based images in-vivo;
   generating, by a computer data processor, an initial organ model being a three-dimensional hollow geometric shell representing an inner surface of an organ within a body, the initial organ model based on a predetermined estimated structure of the imaged organ;
   receiving, by the computer data processor, a user indication of an image captured while the in vivo capsule images a first point of interest to a user identified in the imaged organ;
   determining a position and orientation of the in vivo capsule upon capturing the indicated image of the first point of interest;
   based on the position and orientation of the in vivo capsule, updating, by the computer data processor, the initial model to a customized model, such that a location in the customized model corresponding to the position of the point of interest in vivo reflects the organ size and organ location within the body; and
   based on the customized model and images captured by the in vivo capsule, constructing, by the computer data processor, a three-dimensional visualization of the organ including the images for display to the user.

2. The method of claim 1, wherein determining a position and orientation of the in vivo capsule comprises determining the position of the in vivo capsule relative to fiduciary elements positioned in a navigation system of the in vivo capsule.

3. The method of claim 1, comprising calculating the position of the in vivo capsule in relation to tissue walls of the imaged organ.

4. The method of claim 1, comprising estimating a projection of an image of the organ on the customized model.

5. The method of claim 1, comprising:
   navigating the in vivo capsule to a second point of interest in the imaged organ, receiving an indication of an image captured while the in vivo capsule images the second point of interest,
   determining a position and orientation of the in vivo capsule upon capturing the indicated image of the second point of interest;
   updating the customized model, by setting a second location in the customized model, said second location corresponding to the position of the second point of interest in vivo.

6. The method of claim 5, comprising calculating, based on the customized organ model, a target position for navigating the in vivo capsule, the target position corresponding to the second point of interest.

7. The method of claim 1, comprising:
   automatically navigating the in vivo capsule by selecting a predetermined motion pattern;
   receiving an indication that the in vivo capsule touched the organ walls;
   determining the location of the in vivo capsule when the indication that the in vivo capsule touched the organ walls is received; and
   updating the initial model based on the determined location.

8. The method of claim 1, comprising changing a progress direction of the in vivo capsule upon receiving an indication that the in vivo capsule touched the organ walls.

9. The method of claim 1, comprising estimating a distance between the location of the in vivo capsule and the location of the organ's wall based on the illumination level of an image or a portion of an image.

10. The method of claim 1, comprising calculating visual coverage of the organ imaged by the in vivo capsule, by calculating a percent of the organ that was imaged during the procedure, at a certain point of time.

11. The method of claim 10, comprising verifying, based on the visual coverage of the organ imaged by the in vivo capsule, that the organ under examination has been completely imaged during the imaging procedure.

12. The method of claim 1, comprising determining spatial coordinates of the first point of interest by estimating a distance of the first point of interest in the image from the in vivo capsule.

13. A system for automatic generation of a model of an organ, the system comprising:
   coils to generate a magnetic field;
   a processor to receive light-based images of an organ within a body captured from an in vivo capsule and input accepting a user indication of an image captured while the in vivo capsule images a first point of interest to a user identified in the imaged organ, the processor configured to:
   generate an initial organ model being a three-dimensional hollow geometric shell representing an inner surface of an organ within a body, the initial organ model based on a predetermined estimated structure of the imaged organ;
   receive the indication of an image captured while the in vivo capsule images a first point of interest identified in the imaged organ;
   determine a position and orientation of the in vivo capsule upon capturing the indicated image of the first point of interest; and
   based on the position and orientation of the in vivo capsule, update the initial model to a customized model, such that a location in the customized model corresponding to the position of the point of interest in vivo reflects the organ size and organ location within the body; and
   based on the customized model and images captured by the in vivo capsule, construct a three-dimensional visualization of the organ including the images for display to the user.

14. The system of claim 13, comprising fiduciary elements positioned in a navigation system of the in vivo capsule, wherein the processor is to determine the position and orientation of the in vivo capsule relative to said fiduciary elements.

15. The system of claim 13, wherein the processor is configured to calculate the position of the in vivo capsule in relation to tissue walls of the imaged organ.

16. The system of claim 13, wherein the system further comprises:
   a display to display the visualization to the user.

17. The system of claim 16, wherein the processor is configured to estimate a projection of an image of the organ on the customized model.

18. A method for automatic generation of a model of an in vivo organ, the organ imaged by an in vivo capsule comprising an imager, the method comprising:
- capturing, via the in vivo capsule, light-based images in-vivo;
- generating, by a computer data processor, an initial organ model being a three-dimensional hollow geometric shell representing an inner surface of an organ within an organ within a body;
- receiving a user indication of an image captured while the in vivo capsule images a first point of interest to a user identified in the imaged organ;
- determining a position of the in vivo capsule upon capturing the indicated image of the first point of interest; and
- based on the position and orientation of the in vivo capsule, updating, by the computer data processor, the initial model to a customized model such that a location in the customized model corresponding to the position of the point of interest in vivo reflects the organ size and organ location within the body; and
- based on the customized model and images captured by the in vivo capsule, constructing, by the computer data processor, a three-dimensional visualization of the organ including the images for display to the user.

* * * * *